(12) United States Patent
Sabczynski et al.

(10) Patent No.: US 10,076,296 B2
(45) Date of Patent: Sep. 18, 2018

(54) USER INTERFACE FOR X-RAY POSITIONING

(71) Applicant: KONINKLIJKE PHILIPS N.V., Eindhoven (NL)

(72) Inventors: Jörg Sabczynski, Norderstedt (DE); Sabastian Peter Michael Dries, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 602 days.

(21) Appl. No.: 14/357,299

(22) PCT Filed: Nov. 7, 2012

(86) PCT No.: PCT/IB2012/056227
§ 371 (c)(1),
(2) Date: May 9, 2014

(87) PCT Pub. No.: WO2013/072814
PCT Pub. Date: May 23, 2013

(65) Prior Publication Data
US 2014/0314204 A1  Oct. 23, 2014

Related U.S. Application Data

(60) Provisional application No. 61/559,194, filed on Nov. 14, 2011.

(51) Int. Cl.
*A61B 6/00* (2006.01)
*A61B 6/08* (2006.01)

(52) U.S. Cl.
CPC .............. *A61B 6/4476* (2013.01); *A61B 6/08* (2013.01); *A61B 6/467* (2013.01); *A61B 6/547* (2013.01)

(58) Field of Classification Search
CPC ....... A61B 6/08; A61B 6/587; A61B 66/4476; A61B 6/467
See application file for complete search history.

(56) References Cited

U.S. PATENT DOCUMENTS 6,814,490 B1 * 11/2004 Suhm .................. A61B 6/4405
378/195
2008/0112700 A1   5/2008 Foxenland
(Continued)

FOREIGN PATENT DOCUMENTS

DE   10335037    3/2005
EP    2389863    11/2011
(Continued)

*Primary Examiner* — Dani Fox
(74) *Attorney, Agent, or Firm* — Larry Liberchuk

(57) ABSTRACT

The present invention relates to positioning of an X-ray source. In order to provide an improved user interface for facilitating the X-ray imaging positioning, a transportable handheld planning device (10) for visualizing projected X-ray radiation for medical X-ray imaging is provided, that comprises a first structure (12) for representing a central axis (14) of a projected X-ray radiation (16), and a second structure (18) for representing a cross-sectional area (20) of the projected X-ray radiation. The first structure is manually positionable by a user in relation to an object to be examined. The second structure is adjustable by a user such that the size and proportions of the cross-sectional area are adjustable in relation to the object to be examined. Further, a current spatial position of the first structure and a current size and proportions of the cross-sectional area are detectable by a measurement arrangement (22).

20 Claims, 7 Drawing Sheets

(56) References Cited

U.S. PATENT DOCUMENTS

| | | |
|---|---|---|
| 2009/0278702 A1 | 11/2009 | Graumann et al. |
| 2010/0008467 A1 | 1/2010 | Dussault et al. |
| 2010/0239070 A1 | 9/2010 | Mohr |

FOREIGN PATENT DOCUMENTS

| | | |
|---|---|---|
| WO | WO2004034909 | 4/2004 |
| WO | WO2009146532 | 12/2009 |

\* cited by examiner

USER INTERFACE FOR X-RAY POSITIONING

CROSS-REFERENCE TO PRIOR APPLICATIONS

This application is the U.S. National Phase application under 35 U.S.C. § 371 of International Application Serial No. PCT/IB2012/056227, filed on Nov. 7, 2012, which claims the benefit of U.S. Application Ser. No. 61/559,194, filed on Nov. 14, 2011. These applications are hereby incorporated by reference herein.

FIELD OF THE INVENTION

The present invention relates to a transportable handheld planning device for visualizing projected X-ray radiation for medical X-ray imaging, an X-ray imaging system, and a method for positioning of an X-ray source.

BACKGROUND OF THE INVENTION

To acquire an X-ray projection image, the tube, patient and detector have to be positioned relative to each other. For example, this is performed by a technician as a manual task. An X-ray source may be provided with a light visor such that the technician can see where the actual X-ray beam would be positioned. The light visor projects light from the tube to indicate, for example, centre and collimation of the X-ray beam that will result from the current positioning. Thus, the technician moves the X-ray source, as well as the patient, until a desired spatial relation has been achieved. For example, WO 2004/034909 A1 describes a light pointer for a radiographic device. However, the procedure of positioning may be time-consuming due to the necessary movement of the X-ray source itself.

SUMMARY OF THE INVENTION

Thus, there may be a need to provide an improved user interface for facilitating the X-ray imaging positioning.

The object of the present invention is solved by the subject-matter of the independent claims, wherein further embodiments are incorporated in the dependent claims.

It should be noted that the following described aspects of the invention apply also for the transportable handheld planning device, the X-ray imaging system, as well as the method for positioning of an X-ray source.

According to a first aspect of the present invention, a transportable handheld planning device for visualizing projected, i.e. for example planned or desired, X-ray radiation for medical X-ray imaging is provided. The transportable handheld planning device comprises a first structure for representing a central axis of a projected X-ray radiation, and a second structure for representing a cross-sectional area of the projected X-ray radiation. The first structure is manually positionable by a user in relation to an object to be examined. The second structure is adjustable by a user such that the size and proportions of the cross-sectional area are adjustable in relation to the object to be examined. Further, a current spatial position of the first structure and a current size and proportions of the cross-sectional area are detectable by a measurement arrangement.

The term "cross-sectional area" relates to the shape of the beam in a direction transverse to the central axis, i.e. not only perpendicular, but also in a different angle to the central axis.

The first structure may be a handheld bar.

The X-ray radiation to be visualized may be an X-ray cone beam, for example.

The first structure is a visible materialization of the invisible central axis of the projected or desired X-ray beam.

The measurement arrangement may also be referred to as a position measurement arrangement.

According to an exemplary embodiment, the second structure is provided as a projection unit projecting frame elements indicating the size and proportions of the cross-sectional area, wherein the projection unit is provided on the planning device. In other words, the projection unit may be part of the planning device itself.

According to an exemplary embodiment, the projection unit is formed integrally with the first structure. Thus, a compact handheld device is provided allowing a facilitated handling.

According to an exemplary embodiment, the projection unit comprises adjustable projection settings such that the projected frame elements can be adapted to different sizes and/or different proportions of the cross-sectional area. The current projection settings are transmitted to the measurement arrangement.

For example, by direct interaction with a respective control button, the user can adjust the projected frame elements, i.e. the visualization of the future X-ray beam in a straight-forward, i.e. direct, self explaining and unambiguous manner. By providing the respective projection settings to the measurement arrangement, the current proportions and size, i.e. the shape, are known and can thus be used for further control of an X-ray source and the respective shutter elements, for example.

According to an exemplary embodiment, the projected frame elements can be adapted to different proportions of the cross-sectional area. The adjustment of the size of the cross-sectional area in relation to the object is provided by an adjustment of the distance of the second structure to the object.

For example, by moving the handheld planning device closer to the object, for example a patient, the size of the projected frame will be smaller, and by moving the handheld planning device further away, the size will increase. An input by a respective control interface, for example, is thus only necessary in relation to the proportions, i.e. the form or shape.

According to an exemplary embodiment, the second structure is provided as an adjustable frame structure that can be adapted to different sizes and/or different proportions of the cross-sectional area.

For example, an adaptable frame can be positioned directly on an object, for example on the patient's skin, to represent the desired area to be covered by an X-ray beam. This allows the user to first determine the area to be covered by an X-ray beam, and as a second positioning step, the direction of the central X-ray beam, or central axis of the X-ray beam, can then be determined by a respective alignment of the handheld planning device's first structure. Of course, it is also possible to determine the direction first, and to determine the proportion and size afterwards, or to determine both parameters at the same time.

According to an exemplary embodiment, the first structure is activatable for providing a second function in which it is movable to indicate free space for the movement of an X-ray source. The movement is detectable by the measurement arrangement.

For example, the user can waggle the first structure, or otherwise move it across the free space and the measurement arrangement is thus provided with spatial coordinates of space available for a positioning of equipment, for example the X-ray source. This information can then be used for optimizing the tube's position, for example with respect to skin dose requirements.

According to a second aspect of the present invention, an X-ray imaging system is provided, comprising an X-ray source, an X-ray detector, a motorized support for moving the X-ray source and/or the X-ray detector, a measurement arrangement, and a control unit. Further, a handheld planning device according to one of above described handheld planning devices is provided to define a central axis and a cross-sectional area of a desired X-ray beam in relation to an object to be examined. The measurement arrangement is configured to detect current spatial position data and current size and proportions information of the planning device representing the desired X-ray beam. The measurement arrangement is also configured to detect the spatial relation of the handheld planning device to the X-ray source and/or X-ray detector. The control unit is configured to compute a target position of the X-ray source to provide the desired X-ray beam. The control unit is also configured to activate the motorized support for bringing the X-ray source and/or X-ray detector to a position such that the desired X-ray radiation may be provided detectably.

According to an exemplary embodiment, the current spatial position and orientation of the X-ray source and/or detector is detectable by the measurement arrangement. The control unit computes the movement vectors for bringing the X-ray source and/or X-ray detector into the desired position for the X-ray radiation step.

According to an exemplary embodiment, the X-ray source and/or X-ray detector are provided with a housing comprising a reception. The planning device is storable in the reception such that the X-ray source and/or the X-ray detector movement is trackable with the measurement arrangement.

This provides the further advantage that before or after positioning and determining the direction and proportions of the desired X-ray radiation, the same equipment can also be used for tracking the position of the X-ray source and the X-ray detector. From the respective spatial coordinates, the necessary control command for activating the motorized equipment can then be computed. For example, the reception is provided with a sensor detecting the insertion of the planning device in order to provide a signal to the measurement arrangement that the position data transmitted in the following relates to the X-ray source and/or detector, and not to the positioning of the X-ray beam and the proportions.

According to a third aspect of the present invention, a method for positioning of an X-ray source is provided, comprising the following steps:
a) placing a transportable handheld planning device for visualizing projected, i.e. for example planned or desired, X-ray radiation for medical X-ray imaging such that a first structure represents a central axis of a projected X-ray beam;
b) adjusting current size and proportions of a second structure for representing a cross-sectional area of the projected X-ray beam;
c) detecting the current spatial position of the first structure and the current size and proportions of the cross-sectional area; and
d) activating a motorized X-ray source support to move the X-ray source to a position such that the desired X-ray radiation is provided detectably.

According to a further example, in step d) also, or alternatively, the motorized support can be activated to move the X-ray detector to a position such that the desired X-ray radiation is provided detectably.

According to an aspect of the present invention, an X-ray technician can use the transportable handheld planning device, for example, in form of a token, which may also be referred to as a "magic wand", to indicate the desired position and orientation of the central beam. Further, also the sizes and proportion can be set by the technician. The position and orientation of the transportable handheld planning device is measured with a position measurement device, for example. Afterwards, for example, a ceiling-mounted and motorized X-ray tube suspension system moves the X-ray tube automatically to the desired position. Especially in acquisitions with the detector being provided not in a patient table, but as a so-called wall stand, or being positioned freely as necessary for some projections, or if the patient is immobile in the bed, for example, the positioning of the tube requires deliberate and thus time-consumptive alignment. By providing the transportable handheld planning device according to the present invention, the alignment, when preparing the patient and the equipment to position the X-ray tube according to the protocol for a particular organ, for example, or disease to be imaged, is facilitated. By providing a transportable handheld planning device that is operable by a single hand of the technician, it is also possible to position and arrange the patient at the same time to a desired position.

According to a further aspect, the invisible central axis of the X-ray beam is not only visualized, but also materialized by the handheld planning device. This directly provides the user with the needed information during the positioning. The materialization also helps in targeting for certain organ structures being invisible to the technician while positioning the handheld planning device. However, the technician can simply project the direction of the handheld planning device so-to-speak inside the body structure, thus giving him or her an impression how to adjust the positioning. Further, also the cross-sectional area can be adjusted in a simple way. To reach out for the X-ray source and to align and adjust the source, as is the case with the commonly used light visor equipment, is not needed. Rather, the X-ray source itself can be moved out of the area around the patient during the positioning of the handheld planning device. Thus, the technician can freely move around the patient, and the danger that a collision occurs while positioning the patient, between the technician and the X-ray source, is avoided.

These and other aspects of the present invention will become apparent from and will be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
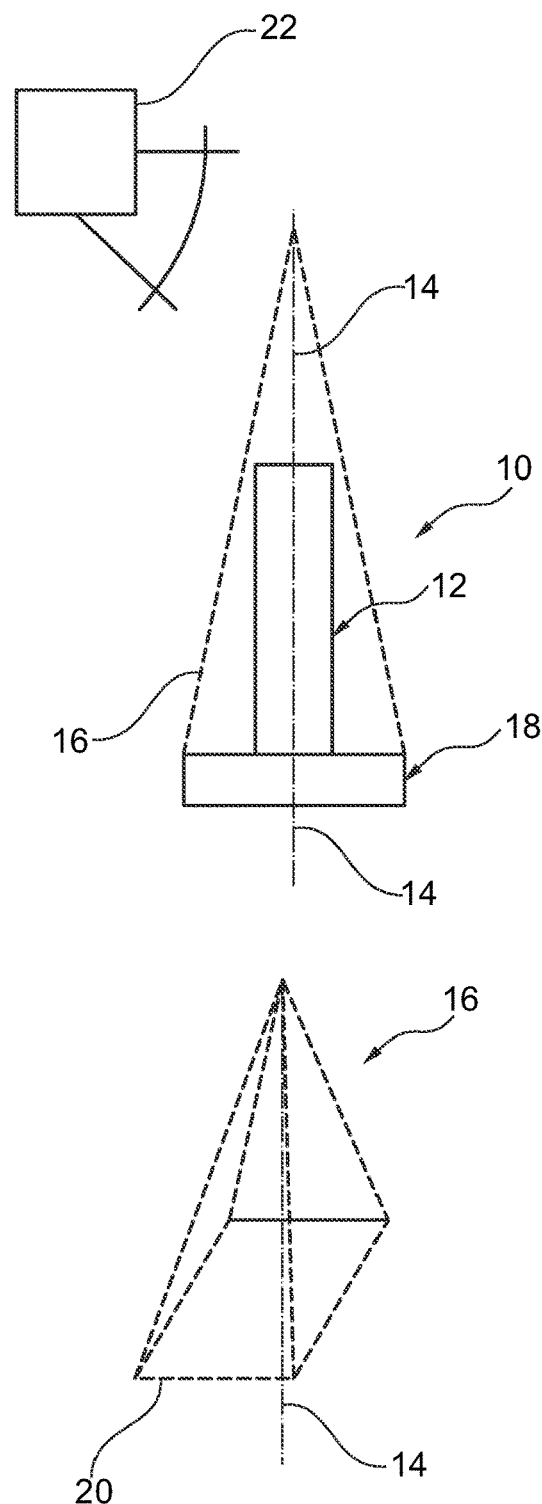
FIG. 1 shows an exemplary embodiment of a transportable handheld planning device according to the present invention.

FIG. 1 shows a transportable handheld planning device 10 for visualizing projected, i.e. for example planned or desired, X-ray radiation for medical X-ray imaging. The handheld planning device 10 comprises a first structure 12 for representing a central axis of a projected X-ray radiation. The central axis is indicated with a first dashed line 14, and the projected X-ray radiation is schematically indicated with two further dashed lines 16. The handheld planning device 10 further comprises a second structure 18 for representing a cross-sectional area of the projected X-ray radiation. The projected X-ray radiation 16 is shown below the transportable handheld planning device 10 for further explanation. The projected X-ray radiation 16 is shown with the central axis 14; and a dashed square 20 schematically indicates the cross-sectional area.

According to the present invention, the first structure 12 is manually positionable by a user in relation to an object to be examined. The second structure 18 is adjustable by a user such that the size and proportions of the cross-sectional area 20 are adjustable in relation to the object to be examined.

A current spatial position of the first structure and current size and proportions of the cross-sectional area are detectable by a measurement arrangement 22.

For example, the first structure 12 may be provided with at least two distinguishable points on a body structure, or a housing, arranged along a central axis of the planning device. The distinguishable points can also be provided in an offset manner in relation to the central axis of the planning device. Further, it is also possible to provide an electromagnetic position measurement system and to provide a single coil on or inside the first structure 12 to determine the respective spatial position. It must be noted that also other detection principles can be provided. For example, for ultrasound, it may be a microphone.

Figure 2:
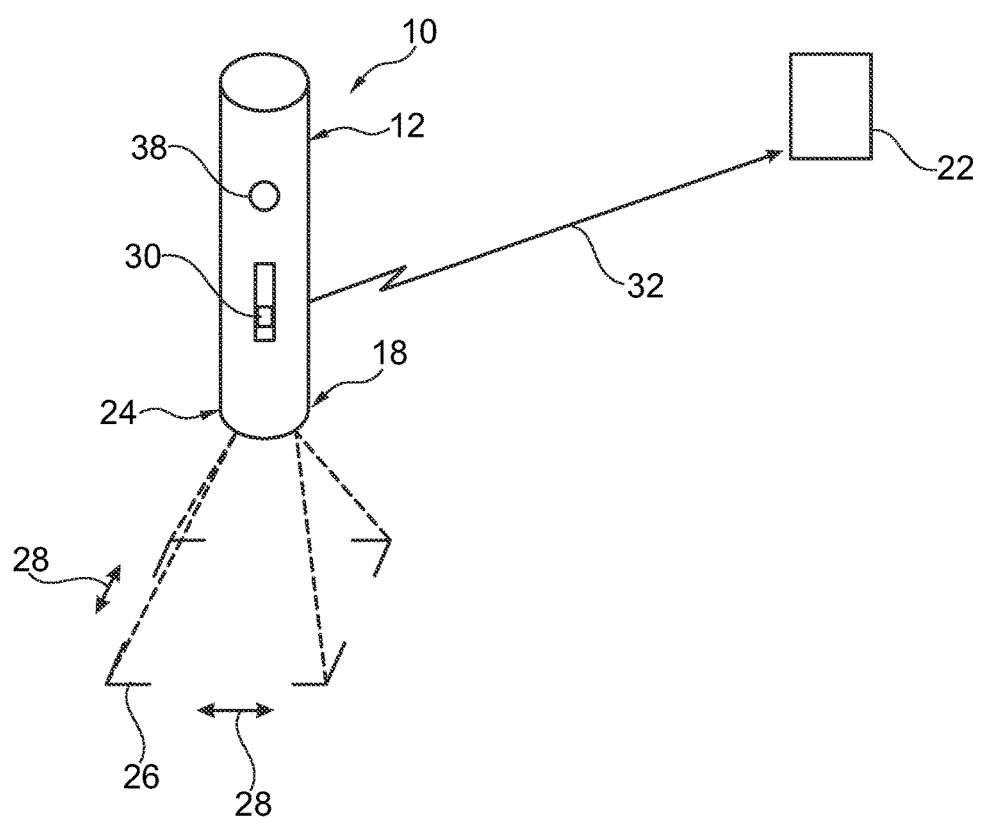
FIG. 2 shows a further exemplary embodiment of a transportable handheld planning device according to the present invention.

FIG. 2 shows an example of the transportable handheld planning device 10, wherein the second structure 18 is provided as a projection unit 24 projecting frame elements 26 indicating the size and proportions of the cross-sectional area. The projection unit 24 is provided on the planning device 10.

For example, the projection unit is formed integrally with the first structure 12, as shown in FIG. 2. However, the projection unit 24 may also be provided as a separate component attached to the first structure 12 (not shown).

According to a further example, also shown in combination with FIG. 2, the projection unit 24 comprises adjustable projection settings such that the projected frame elements can be adapted to different sizes and/or different proportions of the cross-sectional area. This is indicated by two double arrows 28. For example, the projection settings can be adjusted by a slideable interface unit 30 activatable by the user holding the handheld planning device 10. The current projection settings are transmitted to the measurement arrangement 22, for example by wireless communication, as indicated with arrow 32. The projection settings can then be provided to a control unit (not shown), for example.

A further example, although not further shown, is provided, wherein the projected frame elements 26 can be adapted to different proportions of the cross-sectional area, as described above, and, however, the adjustment of the size of the cross-sectional area in relation to the object is provided by an adjustment of the distance of the second structure 18 to the object.

For example, the planning device is moved towards or away from the object to adjust the size of the cross-sectional area in relation to the object.

Figure 3:
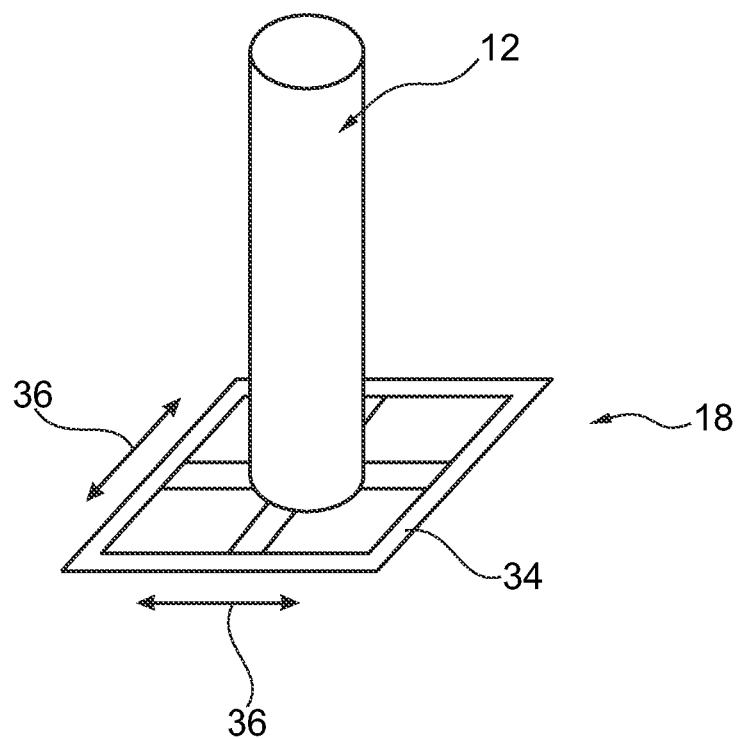
FIG. 3 shows a further exemplary embodiment of a transportable handheld planning device according to the present invention.

FIG. 3 shows a further exemplary embodiment, wherein the second structure 18 is provided as an adjustable frame structure 34 that can be adapted to different sizes and/or different proportions of the cross-sectional area 20. For example, the frame elements can be adjusted, for example in a telescopically manner, which is indicated by double arrows 36. Thus, the size and proportions of the cross-sectional area 20 can be adjusted. It is noted that the frame structure 34 is schematically shown for a square-shaped frame, but can also be provided for other rectangular, other polygonal or otherwise shaped forms.

The second structure 18 and the adjustable frame structure 34 is thus a visible materialization of the invisible cross-sectional area of the projected or desired X-ray beam.

According to a further example, a trigger interface 38 is provided for entering a command by the user for starting with a positioning determination procedure to detect the current spatial position of the first structure and the size and proportions of the cross-sectional area. The trigger interface 38 is exemplarily shown in FIG. 2. It is noted that the trigger interface 38 can also be provided for other examples shown in other figures. It is further noted that although FIG. 2 shows a number of features, these features being described as relating to different examples, the features can of course be provided in the combined manner as shown in FIG. 3, but can also be provided in a separate way, which is why they are referred to as examples.

For example, by activating the trigger interface 38, for example a button, the current situation of the visualization of the projected X-ray radiation may be detected.

According to a further example, the first structure 12 is activatable for providing a second function, in which it is movable to indicate free space for the movement of an X-ray source. The movement is detectable by the measurement arrangement (see also below in relation with FIG. 4).

Figure 4:
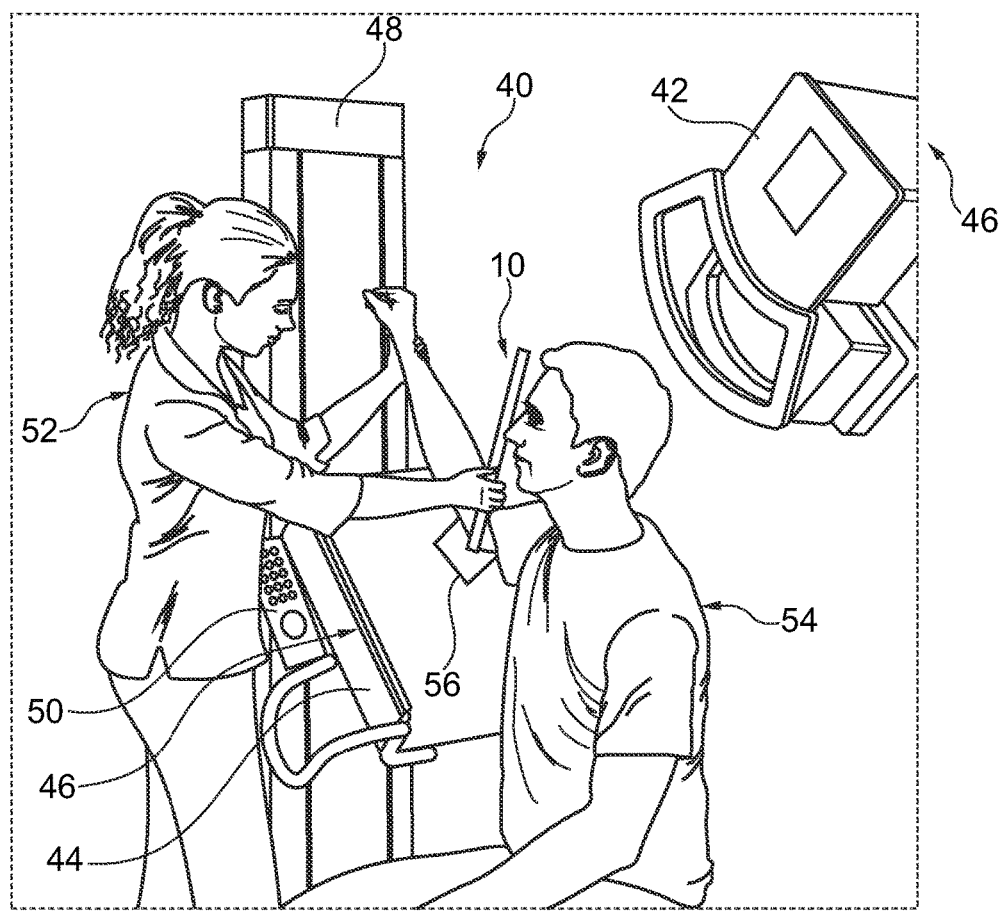
FIG. 4 shows an exemplary embodiment of an X-ray imaging system according to the present invention.

FIG. 4 shows an X-ray imaging system 40, comprising an X-ray source 42, an X-ray detector 44, a motorized support 46 for moving the X-ray source and/or the X-ray detector. Further, a measurement arrangement 48 and a control unit 50 are provided.

Further, a handheld planning device 10 according to one of the above described examples of a transportable handheld planning device is provided to define a central axis and a cross-sectional area of a desired X-ray beam in relation to an object to be examined.

The measurement arrangement 48 is configured to detect current spatial position data and current size and proportions information of the planning device 10 representing the desired X-ray beam, and to detect the spatial relation of the handheld planning device to the X-ray source and/or X-ray detector. The control unit 50 is configured to compute a target position of the X-ray source 42 to provide the desired X-ray beam. The control unit is further configured to activate the motorized support 46 for bringing the X-ray source 42 and/or X-ray detector 44 to a position such that the desired X-ray radiation may be provided.

In the example in FIG. 4, a technician 52 is holding the handheld planning device 10 with one hand, and is further arranging an arm of a patient 54 in a desired position. The handheld planning device indicates the direction of the desired X-ray beam. Further, a dotted frame 56 indicates the desired cross-sectional area of the X-ray beam in relation to the patient. As can be seen, the X-ray source 42 is moved out of the movement range of the patient and the technician. Once the technician has found the desired positioning, the respective spatial information is determined and then used to bring the X-ray source in the respective position such that an X-ray beam with the desired direction and cross-sectional area is provided. Once the determination of the X-ray beam has been completed, the handheld planning device 10 can also be used for a movement in that space which is free for positioning the X-ray tube, for example. The technician can use, for example, the planning device 10 and move the structure between the arm of the patient and the head of the patient to indicate the respective free space. Thus, the occupied space is also determined and the control unit can consider the free space for determining the respective position of the X-ray tube. It is thus possible to prevent a collision of movable parts of the x-ray tube, its housing, or its suspension system with the patient or other equipment. Furthermore, it is thus also possible to provide information in case of a collision of the X-ray beam and other patient's body structures, i.e. penetration of the X-ray beam into other body structures.

According to a further example (not shown), instead of the light projection for the cross-section, an adaptable frame-element is provided, for example on the patients skin.

According to an example (not further shown), the current spatial position and orientation of the X-ray source and/or X-ray detector is detectable by the measurement arrangement 48. The control unit 50 computes the movement vectors for bringing the X-ray source and/or X-ray detector into the desired position for the X-ray radiation step. For example, the control unit computes the movement, i.e. for example a "control unit" as the computer, which controls positioning and measurements. It is noted that in FIG. 4, the control unit 50 is also shown with an interface unit, such as a key pad, for entering data or commands by the user, thus allowing a certain "control" by the user. However, the term control unit refers to the processing unit, or processor arrangement, responsible for computing steps and procedures. The control unit may thus also be provided at another place, for example, also separately.

Therefore, the X-ray source and/or X-ray detector are at least temporarily provided with at least one sensor for providing current spatial position data (not further shown).

For example, the motorized support is permanently equipped with a sensor, e.g. a built-in drive sensor.

Figure 5A:
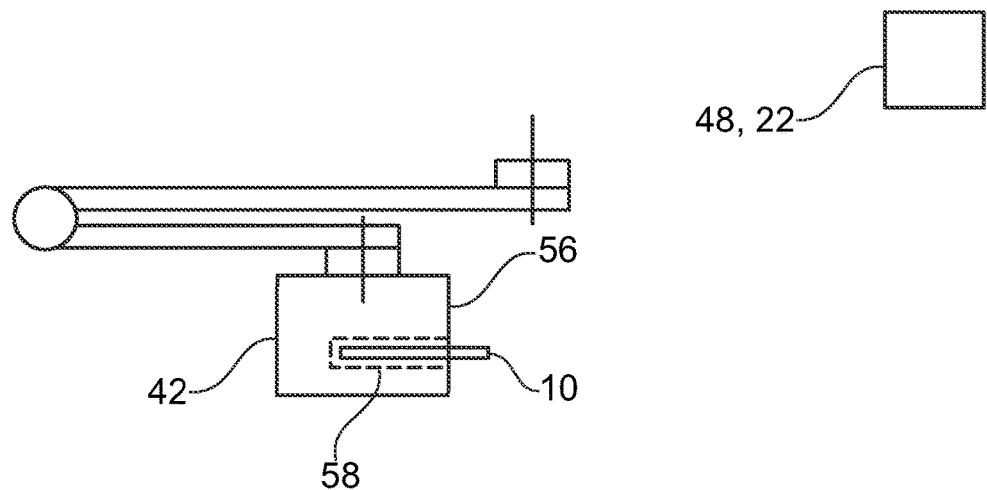
FIGS. 5A and 5B show further exemplary embodiments of an X-ray source and an X-ray detector according to the present invention.

According to the example shown in FIG. 5A, the X-ray source 42 is provided with a housing 56, comprising a reception 58. The planning device 10 is storable in the reception 58 such that the X-ray source movement is trackable with the measurement arrangement 48.

Figure 5B:
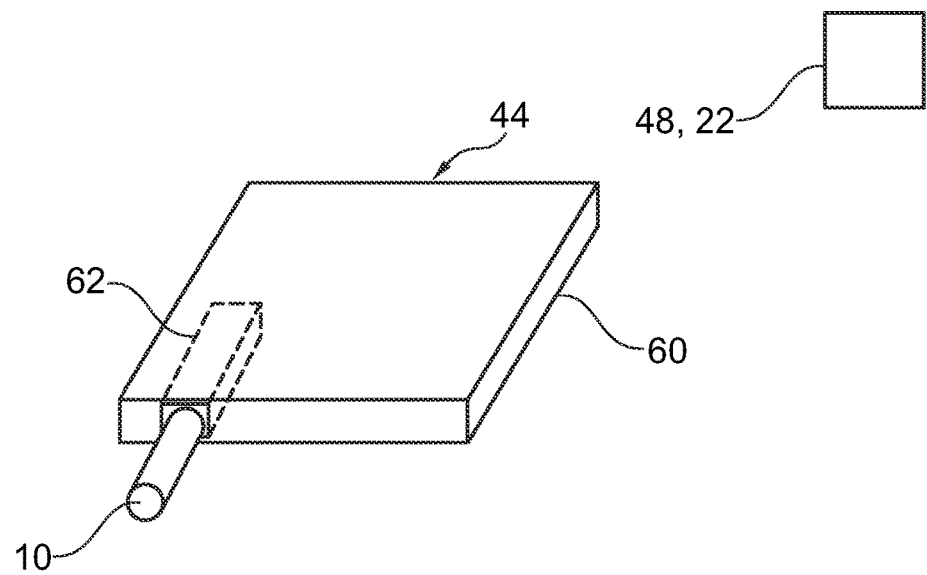

According to the example shown in FIG. 5B, the X-ray detector 44 is provided with a housing 60, comprising a reception 62. The planning device 10 is storable in the reception 62 such that such that the X-ray detector movement is trackable with the measurement arrangement 48.

According to a further example, both, source and detector, or only one of them, are permanently equipped with means to measure their position in space.

According to a further example (not shown), it is provided to update existing X-ray imaging systems with the transportable handheld planning device 10 and the measurement arrangement 22.

It is further also provided according to an example, to update existing housings of an X-ray source or an X-ray detector with an attachable reception for receiving the transportable handheld planning device to determine the respective spatial position.

Figure 6:
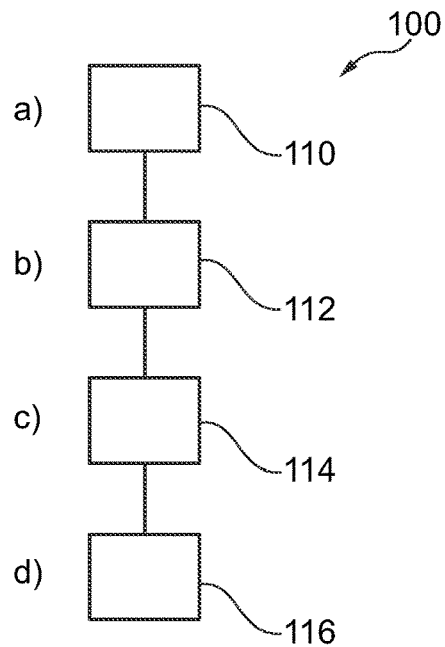
FIG. 6 shows basic steps of an exemplary method according to the present invention.

FIG. 6 shows a method 100 for positioning of an X-ray source. In a first step 110, a transportable handheld planning device is placed for visualizing projected X-ray radiation for medical X-ray imaging such that a first structure represents a central axis of a projected X-ray beam. In a second step 112, current size and proportions of a second structure for representing a cross-sectional area of the projected X-ray beam are adjusted. In a third step 114, the current spatial position of the first structure and the current size and proportions of the cross-sectional area are detected. In a fourth step 116, a motorized X-ray source support is activated to move the X-ray source to a position such that the desired X-ray radiation is provided.

The first step 110 is also referred to as step a), the second step 112 as step b), the third step 114 as step c), and the fourth step 116 as step d).

It is further noted that it is also possible to provide the adjustment of the second step 112 before the aligning the first structure representing the central axis of the first step 110.

Figure 7:
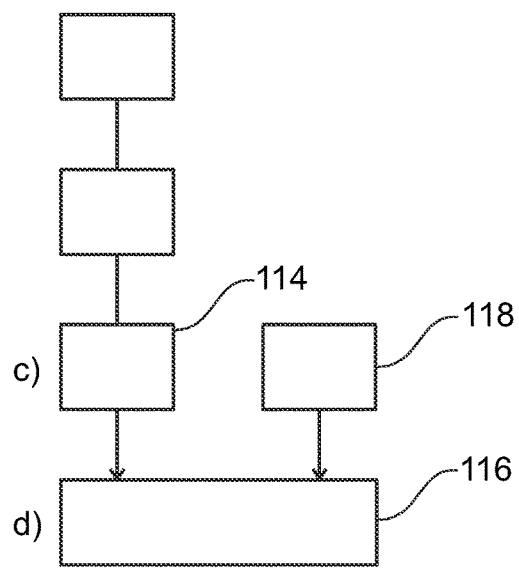
FIG. 7 shows a further exemplary embodiment of a method according to the present invention.

According to a further example, shown in FIG. 7, in addition to step c), current spatial position and orientation of the X-ray source and/or X-ray detector is detected in a fifth step 118 by the measurement arrangement.

Figure 8:
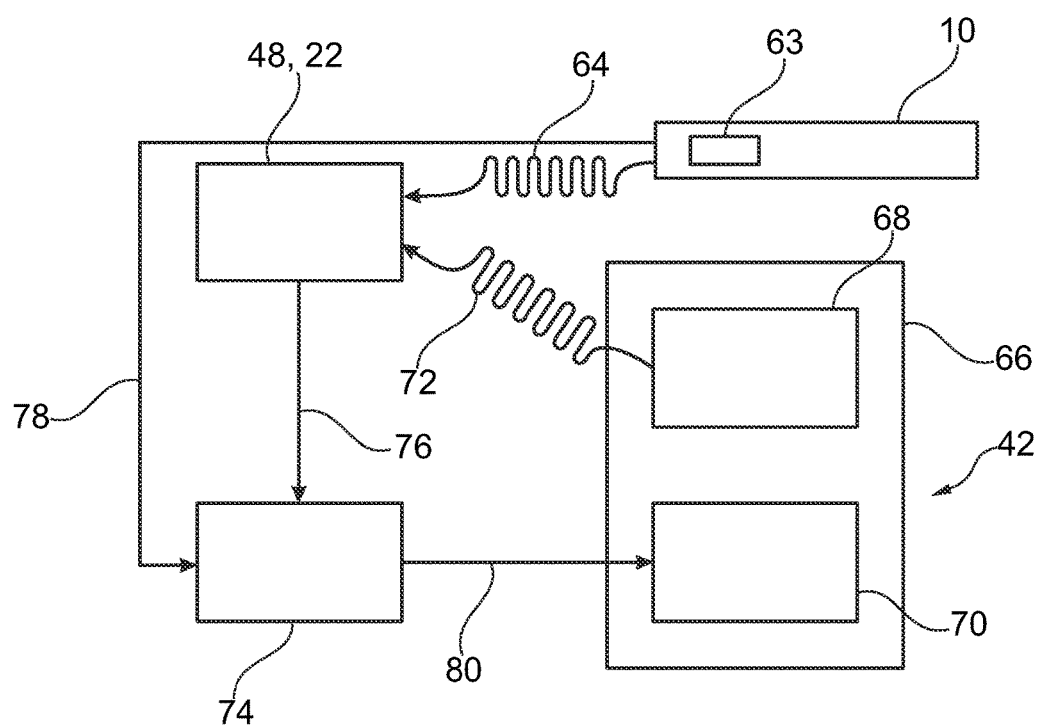
FIG. 8 shows a functional diagram of an exemplary embodiment according to the present invention.

FIG. 8 shows a further example of a functional diagram of the present invention. The transportable handheld planning device 10 is shown with a button 63. Further, the handheld planning device, also referred to as the "magic wand", is in communication 64 with the measurement arrangement 22, 48, which is also referred to as position measurement system. Further, a surrounding rectangular box 66 relates to the X-ray source 42 and comprises a first box 68 representing the tube housing and a second box 70 representing an electronic drive system. Thus, the box 66 refers to the suspension system of the X-ray tube 42. The tube housing 68 is also in communication 72 with the position measurement system 22, 48. The position measurement system 22, 48 provides positions and orientations to a computer 74, wherein the position and orientations are indicated with an arrow 76. A further arrow 78 from the magic wand 10 to the computer 74 indicates a trigger signal. Upon being triggered, the computer provides a target position, indicated with an arrow 80, to the electronic drive system 70.

For example, the position measurement system may be an optical position measurement system or a position measurement system based on electromagnetic detection. The position measurement system may be installed in the X-ray room. It determines the position of the visible transportable handheld planning devices, also referred to as tokens, relative to some coordinate basis. These tokens can be equipped with patterns, which can be recognized by the position measurement system, with retro-reflected markers, for example, or with infrared light emitting diodes. The position measurement system continuously measures the position of the magic wand and, if necessary, of the X-ray tube housing. Of course, the measurement of the position can also be provided in a non-continuous manner, for example with a certain repetition per time frame, or only when triggered, for example. The position and orientation information of the magic wand is then sent to the computer.

The user can press the button 63 on the magic wand 10, when he or she wants to determine and detect the target position and orientation of the central beam and the respective cross-sectional area. A trigger signal is then sent wirelessly to the computer and the computer stores the current position and orientation of the magic wand. The computer then calculates the target position of the tube and initiates the movement of the motorized suspension system to the corresponding position. When the target position is reached, the X-ray technician can take the image from outside the room.

According to a further example (not shown), the camera system of the optical position measurement device can also be mounted to the ceiling-suspension system of a tube, or to the tube housing itself. In the latter case, a reference token needs to be mounted in the X-ray room, or the ceiling-suspension system needs to be calibrated.

The information on the magic wand's position may not be sent continuously from the position measurement system to the computer. Rather, the computer might as well request the necessary information only when the trigger signal comes in.

The user might generate the trigger signal for position recording by a voice command rather than a button press.

The token for position indication may have any shape, not necessarily that of a longitudinal shape as shown in the figures. However, the handheld planning device and the first structure should have such form and proportions, and also such weight, that a user can easily handle the handheld planning device.

In order to aid the positioning of the tube, the position measurement system can be used to close the loop while the motorized suspension system is moving.

As mentioned above, if the motorized suspension system also has built-in drive sensors, i.e. it "knows" where it is, a calibration procedure during setup of the X-ray room can be used to determine the coordinate transformation between position measurement system and suspension system. In this case, closing the loop is not necessary.

A safety mechanism can be built into the motorized suspension system, e.g. such that the suspension can only move, while the X-ray technician presses a safety button.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A transportable handheld planning device for visualizing projected X-ray radiation for medical X-ray imaging, comprising:
    a first structure configured to represent a central axis of a projected X-ray radiation; and
    a second structure configured to represent a cross-sectional area of the projected X-ray radiation;
    wherein the first structure is manually positionable by a user in relation to an object to be examined;
    wherein the second structure is adjustable by a user independently of the first structure such that the size and proportions of the cross-sectional area are adjustable in relation to the object to be examined;
    wherein a current spatial position of the first structure and a current size and proportions of the cross-sectional area are detectable by a measurement arrangement.

2. The planning device according to claim 1, wherein the second structure comprises a projection unit projecting frame elements indicating the size and proportions of the cross-sectional area; wherein the projection unit is provided on the planning device.

3. The planning device according to claim 2, wherein the projection unit is formed integrally with the first structure.

4. The planning device according to claim 2, wherein the projection unit comprises adjustable projection settings such that the projected frame elements can be adapted to different sizes and/or different proportions of the cross-sectional area; wherein the current projection settings are transmitted to the measurement arrangement.

5. The planning device according to claim 2, wherein the projected frame elements are configured to be adapted to different proportions of the cross-sectional area; and wherein the adjustment of the size of the cross-sectional area in relation to the object is provided by an adjustment of the distance of the second structure to the object.

6. The planning device according to claim 1, wherein the second structure comprises an adjustable frame structure that can be adapted to different sizes and/or different proportions of the cross-sectional area.

7. The planning device according to claim 1, further including a trigger interface for entering a command by the user for starting with a positioning determination procedure to detect the current spatial position of the first structure and the size and proportions of the cross-sectional area.

8. The planning device according to claim 1, wherein the first structure is activatable for providing a second function in which it is movable to indicate free space for the movement of an X-ray source; and wherein the movement is detectable by the measurement arrangement.

9. The planning device according to claim 1, further including:
    an X-ray imaging system, comprising:
        an X-ray source;
        an X-ray detector;
        a motorized support for moving the X-ray source and/or the X-ray detector;
        a measurement arrangement; and a control unit;
wherein the measurement arrangement is configured to detect current spatial position data and current size and proportions information of the planning device representing the desired X-ray beam; and to detect the spatial relation of the handheld planning device to the X-ray source and/or X-ray detector;
wherein the control unit is configured to compute a target position of the X-ray source to provide the desired X-ray beam; and
wherein the control unit is configured to activate the motorized support for bringing the X-ray source and/or X-ray detector to a position such that the desired X-ray radiation may be provided detectably.

10. The planning device according to claim 9, wherein the current spatial position and orientation of the X-ray source and/or X-ray detector is detectable by the measurement arrangement; and wherein the control unit computes the movement vectors for bringing the X-ray source and/or X-ray detector into the desired position for the X-ray radiation step.

11. The planning device according to claim 9, wherein the X-ray source and/or X-ray detector are at least temporarily provided with at least one sensor for providing current spatial position data.

12. The planning device according to claim 11, wherein the X-ray source and/or the X-ray detector are provided with a housing comprising a reception and wherein the planning device is storable in the reception such that X-ray source and/or X-ray detector movement is trackable with the measurement arrangement.

13. A method for positioning of an X-ray source and X-ray detector, comprising the following steps:
a) placing a transportable handheld planning device for visualizing projected X-ray radiation for medical X-ray imaging such that a first structure represents a central axis of a projected X-ray beam;
b) adjusting current size and proportions of a second structure independently of the first structure for representing a cross-sectional area of the projected X-ray beam;
c) detecting the current spatial position of the first structure and the current size and proportions of the cross-sectional area; and
d) activating a motorized support to move an X-ray source and/or the X-ray detector to a position such that the projected X-ray radiation is provided and detected.

14. The method according to claim 13, further including: detecting current spatial position and orientation of the X-ray source and/or X-ray detector by the measurement arrangement.

15. The planning device according to claim 2, wherein the projection unit is positioned adjacent an end of the first structure.

16. A transportable handheld planning device configured to visualize projected X-ray radiation for medical X-ray imaging, the device comprising:

a central member configured to represent a central axis of a projected X-ray radiation, the central member being manually positionable by a user in relation to an object to be examined; and
a projection device configured to projecting frame elements indicating the size and proportions of a cross-sectional area of the projected X-ray radiation; the projection device being adjustable by a user independently of the central member such that the size and proportions of the cross-sectional area are adjustable in relation to the object to be examined;
a measurement arrangement configured to detect a current spatial position of the first structure and a current size and proportions of the cross-sectional area.

17. The planning device according to claim 16, wherein the projection device is formed integrally with an end of the first structure.

18. The planning device according to claim 16, wherein the projection device includes an adjustable frame structure with adjustable projection settings configured to allow a user to adjust projected frame elements to different sizes and/or different proportions of the cross-sectional area; the current projection settings being transmitted to the measurement arrangement; and
wherein the projected frame elements are configured to be adapted to different proportions of the cross-sectional area; and the adjustment of the size of the cross-sectional area in relation to the object being provided by an adjustment of the distance of the second structure to the object.

19. The planning device according to claim 16, further including a trigger interface configured to receive a command by the user for starting with a positioning determination procedure to detect the current spatial position of the first structure and the size and proportions of the cross-sectional area.

20. The planning device according to claim 16, further including:
an X-ray imaging system, comprising:
an X-ray source;
an X-ray detector;
a motorized support for moving the X-ray source and/or the X-ray detector;
a measurement arrangement configured to:
detect current spatial position data and current size and proportions information of the planning device representing the desired X-ray beam; and
detect the spatial relation of the handheld planning device to the X-ray source and/or X-ray detector; and
a control unit configured to:
compute a target position of the X-ray source to provide the desired X-ray beam; and
activate the motorized support for bringing the X-ray source and/or X-ray detector to a position such that the desired X-ray radiation may be provided detectably.

* * * * *